(12) United States Patent
Abe (10) Patent No.: US 11,548,999 B2
(45) Date of Patent: Jan. 10, 2023

(54) METHOD FOR MANUFACTURING RESIN BEADS, RESIN BEADS, AND PRODUCT EMPLOYING RESIN BEADS

(71) Applicant: DAINICHISEIKA COLOR & CHEMICALS MFG. CO., LTD., Tokyo (JP)

(72) Inventor: Takashi Abe, Tokyo (JP)

(73) Assignee: Dainichiseika Color & Chemicals Mfg. Co., Ltd., Tokyo (JP)

(*) Notice: Subject to any disclaimer, the term of this patent is extended or adjusted under 35 U.S.C. 154(b) by 0 days.

(21) Appl. No.: 17/597,111

(22) PCT Filed: Jul. 7, 2020

(86) PCT No.: PCT/JP2020/026551
§ 371 (c)(1),
(2) Date: Dec. 27, 2021

(87) PCT Pub. No.: WO2021/006269
PCT Pub. Date: Jan. 14, 2021

(65) Prior Publication Data
US 2022/0267573 A1    Aug. 25, 2022

(30) Foreign Application Priority Data

Jul. 10, 2019    (JP) .............................. JP2019-128253
Apr. 17, 2020    (JP) .............................. JP2020-074304

(51) Int. Cl.
*C08L 1/12*    (2006.01)
*C08J 3/07*    (2006.01)
*C08J 3/09*    (2006.01)
*C08J 3/16*    (2006.01)

(52) U.S. Cl.
CPC ............... *C08L 1/12* (2013.01); *C08J 3/07* (2013.01); *C08J 3/095* (2013.01); *C08J 3/16* (2013.01); *C08J 2301/12* (2013.01); *C08L 2205/18* (2013.01); *C08L 2666/72* (2013.01)

(58) Field of Classification Search
None
See application file for complete search history.

(56) References Cited

U.S. PATENT DOCUMENTS

| 4,968,350 A | | 11/1990 | Bindschaedler et al. |
| 5,244,734 A | * | 9/1993 | Okuma ............... C08B 16/00 428/407 |
| 5,245,024 A | * | 9/1993 | Scarpa ............... B01J 20/24 536/84 |
| 5,972,507 A | * | 10/1999 | Morimoto ........... C08B 16/00 425/10 |
| 2003/0012941 A1 | * | 1/2003 | Fujita ................. C08J 7/02 428/304.4 |
| 2010/0087552 A1 | * | 4/2010 | Shiomi ............... C08J 3/12 516/9 |
| 2016/0303032 A1 | | 10/2016 | Kamei |
| 2022/0142900 A1 | | 5/2022 | Kobayashi et al. |

FOREIGN PATENT DOCUMENTS

| CN | 102911379 | 2/2013 |
| EP | 0309527 | 4/1989 |
| EP | 0750007 | 12/1996 |
| EP | 3943530 | 1/2022 |
| JP | 49-019183 | 2/1974 |
| JP | 50-041954 | 4/1975 |
| JP | 51-090352 | 8/1976 |
| JP | 59-219333 | 12/1984 |
| JP | S63-068645 | 3/1988 |
| JP | 63-095237 | 4/1988 |
| JP | 06-254373 | 9/1994 |
| JP | 2002-363445 | 12/2002 |
| JP | 2005-264120 | 9/2005 |
| JP | 2013-221000 | 10/2013 |
| JP | 2015-117190 | 6/2015 |
| JP | 2017-052961 | 3/2017 |
| JP | 2018-052909 | 4/2018 |
| JP | 2019-031631 | 2/2019 |
| JP | 6694559 | 5/2020 |
| WO | 88/08011 | 10/1988 |
| WO | 2009/123148 | 10/2009 |
| WO | 2015/029790 | 3/2015 |

(Continued)

OTHER PUBLICATIONS

International Search Report, issued in the corresponding PCT application No. PCT/JP2020/026551, dated Sep. 24, 2020, 7 pages (including translation).
Extended European Search Report, issued in the corresponding European Patent Application No. 20837372.0, dated Jul. 29, 2022, 10 pages.
"Novel colored complex cellulose beads", Society of Cosmetic Scientists, 2003, 1 page.
Brazilian Office Action, issued in the corresponding Brazilian Patent Application No. 112022000453-2, dated Jun. 10, 2022, 8 pages.

*Primary Examiner* — Christopher M Rodd
(74) *Attorney, Agent, or Firm* — Hamre, Schumann, Mueller & Larson, P.C.

(57) ABSTRACT

A method for producing resin beads providing various types of products, such as cosmetics, imparted with superior tactile impression, spreadability on skin, transparency, and product stability is provided. The resin beads containing a cellulose derivative as a main component can replace resin particles composed of a synthetic material derived from petroleum. The production method includes: preparing a suspension containing oil droplets containing the cellulose derivative and an organic solvent by mixing an oil phase containing the cellulose derivative and an organic solvent dissolving the cellulose derivative and having a water-solubility of 0.1 to 50.0 g, with an aqueous phase containing a dispersion stabilizer; and contracting the oil droplets by adding water to the suspension, satisfying expression (A) below as defined in the specification, until a content of the organic solvent in the suspension becomes equal to or less than the water-solubility of the organic solvent: $(W/S)/T \leq 1.00$ . . . (A).

18 Claims, 3 Drawing Sheets

(56) References Cited

FOREIGN PATENT DOCUMENTS

| WO | 2016/013568 | 1/2016 |
|----|-------------|--------|
| WO | 2019/156116 | 8/2019 |
| WO | 2020/188698 | 9/2020 |

\* cited by examiner

METHOD FOR MANUFACTURING RESIN BEADS, RESIN BEADS, AND PRODUCT EMPLOYING RESIN BEADS

TECHNICAL FIELD

The present invention relates to a method for producing resin beads containing a cellulose derivative as a main component, resin beads produced by the production method, and products, such as cosmetics, obtained using the resin beads.

BACKGROUND ART

In the past, resin beads have been used in various fields, such as a matting agent, a slipping agent, and an antiblocking agent, from the properties derived from the spherical shape. Further, various resin powders (resin particles), such as resin beads, have been used in order to improve the properties, such as spreadability, of cosmetics for makeup. However, materials for forming resin beads to be blended in cosmetics have been changing from synthetic materials derived from petroleum to natural materials due to the problems and the like, such as marine pollution caused by microplastics, in recent years.

For example, powdery cellulose useful as a scrubbing agent has been proposed as spherical resin particles composed of a natural material (Patent Literature 1). Further, cellulose derivative fine particles (Patent Literature 2) which are used for a diagnostic drug and a spherical cellulose powder (Patent Literature 3) which is used for cosmetics have been proposed. Furthermore, porous cellulose particles and the like which are used as a filler for chromatography have been proposed (Patent Literatures 4 and 5).

CITATION LIST

Patent Literature

Patent Literature 1: Japanese Patent Laid-Open No. 2018-052909
Patent Literature 2: International Publication No. WO 2009/123148
Patent Literature 3: Japanese Patent Laid-Open No. 2013-221000
Patent Literature 4: International Publication No. WO 2016/013568
Patent Literature 5: International Publication No. WO 2015/029790

SUMMARY OF INVENTION

Technical Problem

However, the powdery cellulose and the like proposed in Patent Literatures 1, 2, 4, and 5 do not have a suitable particle diameter as a material to be blended in cosmetics for makeup or skin care. In addition, copper ammonia needs to be used when the cellulose derivative fine particles proposed in Patent Literature 2 are produced, and therefore the cellulose derivative fine particles cannot necessarily be said to be suitable as a material for cosmetics in which heavy metals are desired to be reduced as much as possible.

Further, the spherical cellulose powder and the like proposed in Patent Literatures 3 to 5 have a low degree of sphericity, and the particle surface thereof is not so flat. For this reason, the spreadability on the skin cannot be said to be satisfactory so much when the spherical cellulose powders and the like are blended in cosmetics, so that rough surfaces have been likely to be felt. In addition, light scattering is likely to occur due to the roughness of the particle surfaces, and therefore the feel of the cosmetics has been likely to change significantly accompanied by changes in wetting of the powder.

Furthermore, porous cellulose particles and the like proposed in Patent Literatures 4 and 5 are likely to adsorb moisture because they are porous. For this reason, when the porous cellulose particles and the like are blended in cosmetics, the cosmetics themselves are likely to be made unstable, and therefore the porous cellulose particles and the like cannot necessarily be said to be suitable as a material for cosmetics.

The present invention has been completed in view of the problems of such conventional techniques, and an object of the present invention is to provide a method for producing resin beads which can provide various types of products, such as cosmetics, imparted with superior tactile impression, spreadability on the skin, transparency, and product stability, and which can be substituted for resin particles composed of a synthetic material derived from petroleum. Another object of the present invention is to provide: resin beads which can provide various types of products, such as cosmetics, imparted with superior tactile impression, spreadability on the skin, transparency, and product stability, and which can be substituted for resin particles composed of a synthetic material derived from petroleum; and various types of products, such as cosmetics, using the resin beads.

Solution to Problem

That is, according to the present invention, a method for producing resin beads, described below, is provided.

[1] A method for producing resin beads comprising a cellulose derivative as a main component, the method comprising:

a suspension preparation step of mixing an oil phase comprising the cellulose derivative and an organic solvent that dissolves the cellulose derivative, the organic solvent having a solubility to 100 g of water (water-solubility) at 25° C. of 0.1 to 50.0 g, and an aqueous phase comprising a dispersion stabilizer, thereby preparing a suspension comprising oil droplets comprising the cellulose derivative and the organic solvent; and an oil droplet contraction step of adding water to the suspension, thereby contracting the oil droplets, wherein in the oil droplet contraction step, the water is added to the suspension in such a way as to satisfy the following expression (A) until a content of the organic solvent in the suspension becomes equal to or less than the water-solubility of the organic solvent:

$(W/S)/T \leq 1.00$     (A), wherein

W: an addition amount of water (parts by mass),
S: an amount of the suspension (parts by mass), and
T: a time (minutes) required for addition.

[2] The method for producing resin beads according to [1], being a method for producing the resin beads having a degree of sphericity of 0.95 or more as measured and calculated according to the following procedure: [Procedure of measuring and calculating the sphericity]: a SEM image of the resin beads, taken with a scanning electron microscope, is subjected to image analysis, and a degree of circularity C of each resin bead is calculated from the following formula (1) to determine an arithmetic average value of the degrees of circularity C of arbitrarily selected 100 or more resin beads as the degree of sphericity of the resin beads;

$$C=(4\pi S)/(L^2)$$ (1), wherein

S represents a projected area of each resin bead in the SEM image, and L represents a length of an outer peripheral part of the resin bead in the SEM image.

[3] The method for producing resin beads according to [2], wherein a liquid amount of the water added to the suspension is 0.5 times or more based on a liquid amount of the suspension on a mass basis.

[4] The method for producing resin beads according to any one of [1] to [3], wherein the aqueous phase further comprises a second organic solvent.

[5] The method for producing resin beads according to any one of [1] to [4], wherein a liquid amount of the aqueous phase is 3.0 times or less based on a liquid amount of the oil phase on a mass basis.

[6] The method for producing resin beads according to any one of [1] to [5], wherein the cellulose derivative is at least one selected from the group consisting of cellulose acetate, cellulose acetate butyrate, cellulose acetate propionate, and ethyl cellulose.

[7] The method for producing resin beads according to any one of [1] to [5], wherein the cellulose derivative is cellulose acetate having an acetylation degree of 60% or less.

[8] The method for producing resin beads according to any one of [1] to [7], wherein an acetone solution containing 6% by mass of the cellulose derivative has a viscosity of 200 mPa·s or less.

[9] The method for producing resin beads according to any one of [1] to [8], wherein the organic solvent is at least one selected from the group consisting of a ketone-based solvent, an ester-based solvent, an alcohol, a glycol, an ether-based solvent, a halogenated alkyl, and a nitrated alkyl.

[10] The method for producing resin beads according to any one of [1] to [9], wherein a liquid amount of the organic solvent is 2.0 times or more based on an amount of the cellulose derivative on a mass basis.

[11] The method for producing resin beads according to any one of [1] to [10], wherein the dispersion stabilizer is a water-soluble polymer.

[12] The method for producing resin beads according to any one of [1] to [11], wherein a content of the dispersion stabilizer in the aqueous phase is 30% by mass or less.

[13] The method for producing resin beads according to any one of [1] to [12], wherein the resin beads having a volume average particle diameter of 50 μm or less are obtained.

[14] The method for producing resin beads according to any one of [1] to [13], wherein the resin beads having a solid structure in which 90% by volume or more of an inside of the solid structure is filled with the cellulose derivative are obtained.

[15] The method for producing resin beads according to any one of [1] to [14], wherein the oil phase further comprises at least any one of a pigment and a dye.

[16] The method for producing resin beads according to any one of [1] to [14], wherein the oil phase further comprises: a pigment; and at least any one of a surfactant and a polymer dispersant.

[17] The method for producing resin beads according to [15] or [16], wherein the pigment is silicone-treated.

[18] The method for producing resin beads according to any one of [1] to [17], wherein the oil phase further comprises at least any one of an ultraviolet absorbing agent and an ultraviolet scattering agent.

Further, according to the present invention, resin beads and a product, described below, are provided.

[19] Resin beads produced by the production method according to any one of [1] to [18].

[20] A product of any one of a cosmetic, a dermatological preparation, a paint, a shaped article, a film, a coating agent, and a resin composition, the product comprising resin beads, wherein the resin beads are the resin beads according to [19].

Advantageous Effects of Invention

The present invention can provide a method for producing resin beads which can provide various types of products, such as cosmetics, imparted with superior tactile impression, spreadability on the skin, transparency, and product stability, and which can be substituted for resin particles composed of a synthetic material derived from petroleum.

In addition, the present invention can provide: resin beads which can provide various types of products, such as cosmetics, imparted with superior tactile impression, spreadability on the skin, transparency, and product stability, and which can be substituted for resin particles composed of a synthetic material derived from petroleum; and various types of products, such as cosmetics, using the resin beads.

DESCRIPTION OF EMBODIMENTS

Hereinafter, embodiments of the present invention will be described, but the present invention is not limited to the following embodiments. Note that various physical property values in the present specification are values at normal temperature (25° c.) unless otherwise noted.

The present inventors have conducted various studies on resin beads which can provide various types of products, such as cosmetics, imparted with superior tactile impression, spreadability on the skin, transparency, and product stability, and which is composed of a natural material, and the method for producing the resin beads. As a result, by adopting the constitution described below, the present inventors have found that resin beads which are substantially formed with a natural material, and which can provide various types of products, such as cosmetics, imparted with the above-described various properties can be produced. That is, the method for producing resin beads of the present invention is a method for producing resin beads containing a cellulose derivative as a main component, the method including a step (suspension preparation step) of mixing an oil phase (first liquid) containing the cellulose derivative and an organic solvent that dissolves the cellulose derivative, and an aqueous phase (second liquid) containing a dispersion stabilizer, thereby preparing a suspension containing oil droplets containing the cellulose derivative and the organic solvent.

Figure 1:
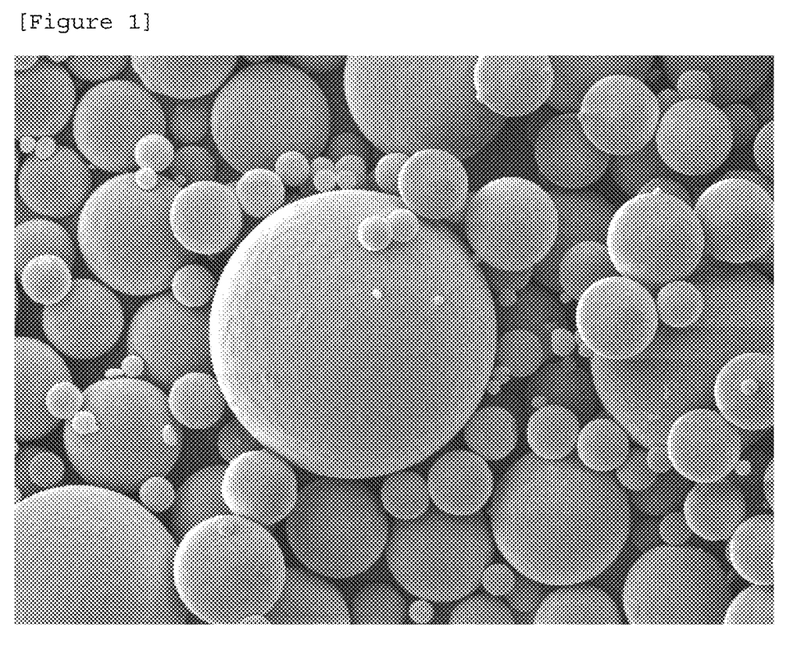
FIG. 1 is an electron micrograph showing a state of surfaces of resin beads produced in Example 1.
Figure 2:
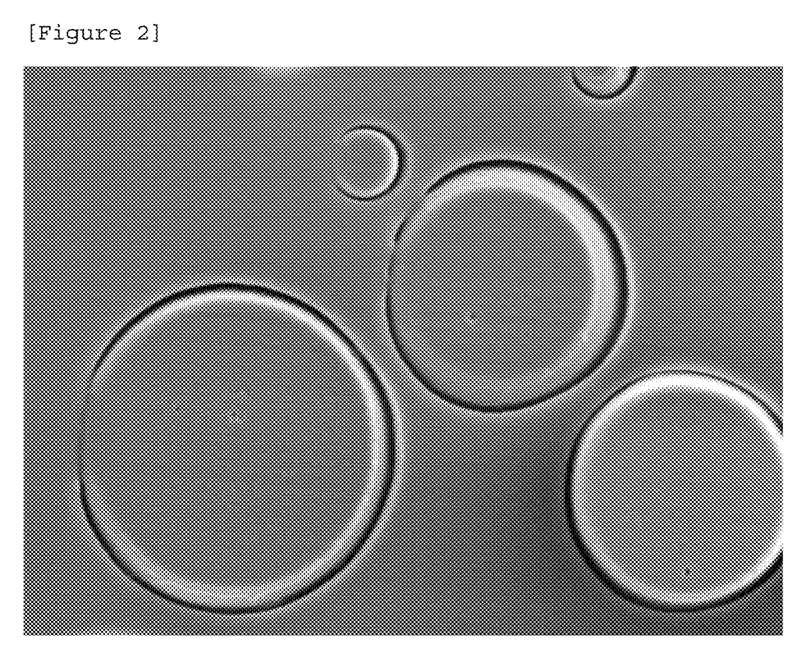
FIG. 2 is an electron micrograph showing a state of sections of resin beads produced in Example 1.

In the suspension preparation step, the oil phase containing a cellulose derivative and an organic solvent that dissolves the cellulose derivative, and an aqueous phase containing a dispersion stabilizer are mixed. By mixing and, if necessary, stirring the oil phase and the aqueous phase, a suspension in which oil droplets containing the cellulose derivative and the organic solvent are dispersed in water can be obtained. These oil droplets are present in a dispersed state in water, and therefore the organic solvent in the oil droplets transfers gradually into water. The oil droplets contract accompanied by the transfer of the organic solvent, so that the cellulose derivative dissolved in the solvent precipitates gradually. The precipitated cellulose derivative grows while retaining flat surfaces as shown in FIG. 1. Finally, the precipitated cellulose derivative is fixed, and substantially solid resin beads as shown in FIG. 2 are formed. Whether the contraction of the oil droplets has occurred or not can be decided by analyzing an image observed using an optical microscope, an electron microscope, or the like. When such contraction of the oil droplets occurs, resin beads which have high sphericity (degree of sphericity), which are substantially solid, which have flat surfaces, and which have a desired particle diameter can thereby be obtained. By using the resin beads obtained in this way, various types of products, such as cosmetics, imparted with superior tactile impression, spreadability on the skin, transparency, and product stability can be provided.

The cellulose derivative is obtained by modifying cellulose having three hydroxy groups in one unit. The cellulose derivative may be the one obtained by substituting one hydroxy group in cellulose with a particular substituent, the one obtained by substituting two hydroxy groups with a particular substituent, or the one obtained by substituting three hydroxy groups with a particular substituent. The structure of the substituent may be any of a linear structure, a branched structure, and a cyclic structure. In addition, the cellulose derivative may be a salt. A cellulose derivative appropriately selected from known cellulose derivatives taking the purpose of use of the resin beads into consideration can be used as the cellulose derivative. Among the cellulose derivatives, cellulose esters which are used, as a natural cellulose derivative, for products, such as cosmetics, are preferable.

Specific examples of the cellulose derivative include methyl cellulose, ethyl cellulose, cellulose acetate, cellulose acetate butyrate, cellulose acetate propionate, nitrocellulose, hydroxypropyl methyl cellulose, hydroxyethyl methyl cellulose, hydroxypropyl cellulose, hydroxypropyl methyl cellulose phthalate, hypromellose acetate succinate, carboxymethyl cellulose, and cellulose glycolic acid ether. Note that examples of the cellulose acetate include acetyl cellulose, diacetyl cellulose, and triacetyl cellulose. These cellulose derivatives can be used singly, or two or more of these cellulose derivatives can be used in combination.

Among the cellulose derivatives, specific examples of the cellulose esters include methyl cellulose, ethyl cellulose, cellulose acetate, diacetyl cellulose, triacetyl cellulose, cellulose acetate butyrate, and cellulose acetate propionate. The viscosity of an acetone solution containing 6% by mass of the cellulose derivative is preferably 200 mPa·s or less. In addition, the cellulose derivative is preferably cellulose acetate having an acetylation degree of 60% or less.

As the organic solvent (first organic solvent) contained in the oil phase, a known organic solvent which can dissolve the cellulose derivative can be used. As the specific examples of the organic solvent, ester-based solvents, such as methyl formate, ethyl formate, methyl acetate, ethyl acetate, and butyl acetate; ketone-based solvents, such as acetone, methyl ethyl ketone, methyl isobutyl ketone, and cyclohexane; alcohols, such as ethanol and n-butanol; ether-based solvents, such as ethyl cellosolve, butyl cellosolve, and ethylene glycol diethyl ether; glycol ether-based solvents, such as dipropylene glycol monomethyl ether; glycol ester-based solvents, such as propylene glycol monomethyl ether acetate; chlorine-based solvents, such as methylene chloride, chloroform, and tetrachloroethane; nitromethane; propylene carbonate, and the like can be used. These organic solvents can be used singly, or two or more of these organic solvents can be used in combination.

The organic solvent is preferably a ketone-based solvent, an ester-based solvent, an alcohol, a glycol, an ether-based solvent, a halogenated alkyl, or nitrated alkyl. Among others, the organic solvent is further preferably methyl ethyl ketone, ethyl acetate, butanol, propylene glycol monobutyl ether, or propylene glycol monomethyl ether acetate.

The organic solvent in the oil droplets contained in the suspension transfers gradually to the aqueous phase. However, when the water-solubility of the organic solvent is too high, the organic solvent is likely to transfer rapidly from the oil droplets into the aqueous phase, and therefore the oil droplets contract, so that the resin beads to be formed may be difficult to have a perfectly spherical shape, or a flat surface may be difficult to form. In addition, when the water-solubility of the organic solvent is too high, the aqueous phase is likely to penetrate partially into the oil droplets, so that solid resin beads may be difficult to form. On the other hand, when the water-solubility of the organic solvent is too low, there is a tendency that the transfer speed of the organic solvent from the oil droplets to the aqueous phase is lowered, and a large amount of aqueous phase needs to be used, so that the resin beads may be disadvantageous in terms of production costs. In addition, when the water-solubility of the organic solvent is too low, the organic solvent may be likely to be left in the resin beads. For this reason, the solubility to 100 g of water (water-solubility) of the organic solvent at 25° C. is 0.1 to 50.0 g, preferably 0.5 to 40.0 g, and still more preferably 1.0 to 30.0 g.

The liquid amount of the organic solvent contained in the oil phase (first liquid) is preferably 2.0 times or more, and more preferably 2.5 to 15.0 times based on the amount of the cellulose derivative on a mass basis. If the liquid amount of the organic solvent in the oil phase is too small, the cellulose derivative is likely to precipitate rapidly when the organic solvent in the oil droplets transfers into the aqueous phase. For this reason, resin beads to be obtained may be difficult to have a perfectly spherical shape, or a flat surface may be difficult to form.

The aqueous phase that is used in the suspension preparation step is a liquid (second liquid) in which a dispersion stabilizer is dissolved in water, such as deionized water. As the dispersion stabilizer, water-soluble polymers, such and water-soluble cellulose, polyvinyl alcohol, and sodium polyacrylate; and inorganic salts, such as hydroxyapatite, tribasic calcium phosphate, and calcium carbonate, can be used. These dispersion stabilizers can be used singly, or two or more of these dispersion stabilizers can be used in combination. Among these dispersion stabilizers, a water-soluble polymer, such as water-soluble cellulose, polyvinyl alcohol, or sodium polyacrylate, is preferably used.

To suppress break or coalescence of the oil droplets in the suspension during transportation, it is preferable that the type and concentration of the dispersion stabilizer which is used in the aqueous phase be set appropriately. The content of the dispersion stabilizer in the aqueous phase is preferably 30% by mass or less, and more preferably 1 to 20% by mass.

It is preferable that the aqueous phase further contain a second organic solvent. The organic solvent (first organic solvent) in the oil phase may transfer rapidly into the aqueous phase depending on the type. Accordingly, by mixing the aqueous phase containing the second organic solvent with the oil phase, the rapid transfer of the first organic solvent in the oil phase into the aqueous phase can be suppressed, so that the resin beads having a higher degree of sphericity and having a further flat surface can be produced. As the second organic solvent, the same organic solvent as the previously mentioned organic solvent (first organic solvent) which is used in the oil phase, including a preferred first organic solvent, can be used. Note that the first organic solvent and the second organic solvent may be of the same type or of different types.

In the suspension preparation step, the suspension is prepared by mixing the oil phase and the aqueous phase. To mix the oil phase and the aqueous phase, the oil phase may be added to the aqueous phase under stirring, or the aqueous phase may be added to the oil phase under stirring. If necessary, the particle diameters of the oil droplets to be formed are preferably adjusted using an emulsification apparatus, such as a disper or a homogenizer. The particle diameters of the oil droplets to be formed can easily be adjusted by, for example, changing the number of revolutions of the homogenizer to adjust the shear force. As a result, the particle diameters of the resultant resin beads can appropriately be adjusted in such a way as to fall within a desired range.

The liquid amount of the aqueous phase is preferably set to 3.0 times or less, and more preferably 0.2 to 2.8 times based on the liquid amount of the oil phase on a mass basis. By setting the liquid amount of the aqueous phase to the above-described range, the rapid transfer of the organic solvent in the oil droplets into the aqueous phase can be suppressed, so that the resin beads having a higher degree of sphericity and having a further flat surface can be produced.

The method for producing resin beads of the present invention includes a step (oil droplet contraction step) of adding water to the suspension, thereby contracting the oil droplets. By adding water to the suspension, the oil droplets in the suspension can quickly be contracted. The liquid amount of water to be added to the suspension is preferably 0.5 times or more, and more preferably 1 to 40 times based on the liquid amount of the suspension on a mass basis.

In the oil droplet contraction step, water is added to the suspension over a certain amount of time. By adding water to the suspension over a certain amount of time, the rapid transfer of the organic solvent in the oil droplets into the aqueous phase can be suppressed, so that the resin beads having a high degree of sphericity and having a flat surface can be produced.

The cellulose derivative derived from natural products usually contains a large number of components having a molecular weight and the like different from each other, and the composition thereof is different depending on the difference in the place of production and the material type of the cellulose to be a raw material. For this reason, the solubility of the cellulose derivative is not constant, and in the aqueous phase of the suspension, the cellulose derivative is present in a state of dissolving slightly. When water is added to the suspension in the oil droplet contraction step, the cellulose derivative which has dissolved in the aqueous phase of the suspension may precipitate. The cellulose derivative in the aqueous phase is more likely to precipitate when the speed of adding water to the suspension is faster. It is considered that this is due to a rapid concentration change in the aqueous phase which dissolves the organic solvent. The cellulose derivative which has precipitated rapidly is adsorbed onto the resin beads to lower the flatness of the surfaces, and the resin beads are likely to aggregate due to the adsorbed cellulose derivative, so that the aggregation may lower the tactile impression of the resin beads. In contrast, it is considered that by adding water to the suspension over a certain amount of time, lowering of the flatness and aggregation are suppressed, so that the resin beads which have a flat surface, which are unlikely to aggregate, and which give satisfactory tactile impression can be produced.

The present inventors have conducted studies on the condition for contracting the oil droplets smoothly and obtaining the resin beads which have a high degree of sphericity, which have a flat surface, and which give satisfactory tactile impression. As a result, the present inventors have found that it is important to control the relation among the amount of the suspension (S; parts by mass), the addition amount of water (W; parts by mass), and the time required for addition of water (T; minutes) suitably. Specifically, water is added to the suspension in such a way as to satisfy the following expression (A) until the content of the organic solvent in the suspension becomes equal to or less than the water-solubility of the organic solvent. That is, the time required for addition of water is set taking the ratio of the addition amount of water to the amount of the suspension (W/S) into consideration. Thereby, the rapid transfer of the organic solvent in the oil droplets into the aqueous phase is suppressed and the resin beads having a high degree of sphericity and having a flat surface can be produced.

$$(W/S)/T \leq 1.00 \quad (A)$$

W: addition amount of water (parts by mass)
S: amount of suspension (parts by mass)
T: time (minutes) required for addition Water is preferably added to the suspension in such a way as to satisfy the following expression (B), water is more preferably added to the suspension in such a way as to satisfy the following expression (C), and water is particularly preferably added to the suspension in such a way as to satisfy the following expression (D), until the content of the organic solvent in the suspension becomes equal to or less than the water-solubility of the organic solvent. The lower limit of the value of "(W/S)/T" is not particularly limited but may be 0.01 or more when work efficiency and the like are taken into consideration. In addition, water is preferably added to the suspension over 30 minutes or longer, water is more preferably added over 45 minutes or longer, and water is particularly preferably added over 60 to 150 minutes.

$$(W/S)/T \leq 0.50 \quad (B)$$

$$(W/S)/T \leq 0.20 \quad (C)$$

$$(W/S)/T \leq 0.10 \quad (D)$$

W: addition amount of water (parts by mass)
S: amount of suspension (parts by mass)
T: time (minutes) required for addition Note that after water is added to the suspension in such a way as to satisfy the expression (A), and the content of the organic solvent in the suspension becomes equal to or less than the water-solubility of the organic solvent, there is no need to add water to the suspension over time. That is, water may be added rapidly, or water may be added over a certain amount of time.

The resin beads may contain at least any one of a pigment and a dye according to the application. To obtain the resin beads containing a pigment or a dye, the suspension may be prepared using, for example, the oil phase further containing at least any one of the pigment and the dye. Examples of the pigment include metal oxides, such as titanium dioxide, zinc oxide, Bengala, yellow iron oxide, and black iron oxide, and besides, Food Yellow No. 4, Food Red No. 202, and Food Blue No. 1, which are Japanese names of certified colors, and carbon black. In addition, extender pigments, such as mica, talc, kaolin, and calcium carbonate, can also be used. Examples of the dye include Food Red No. 104, Food Yellow No. 5, and Food Blue No. 1.

When the resin beads containing a pigment is produced, the oil phase further containing a pigment and at least any one of a surfactant and a polymer dispersant is preferably used. That is, it is preferable to make a state in which the pigment is dispersed in the oil phase in advance. In addition, the pigment in the oil phase is preferably silicone-treated.

The resin beads may contain at least any one of an ultraviolet absorbing agent and an ultraviolet scattering agent according to the application. To obtain the resin beads containing an ultraviolet absorbing agent or an ultraviolet scattering agent, the suspension may be prepared using, for example, the oil phase further containing at least any one of the ultraviolet absorbing agent and the ultraviolet scattering agent. Examples of the ultraviolet absorbing agent and the like include fine particle titanium oxide, fine particle zinc oxide, a cinnamic acid-based ultraviolet absorbing agent, and a dibenzoylmethane-based ultraviolet absorbing agent.

After the suspension preparation step, unnecessary components, such as the dispersion stabilizer, are removed by, for example, subjecting the produced resin beads to filtration and washing. Subsequently, washing is repeated plural times as necessary, and drying and a cracking treatment are then performed, so that the objective resin beads can be obtained.

According to the production method of the present invention, the resin beads having a volume average particle diameter of 50 μm or less, and preferably 0.5 to 40 μm, can be obtained. That is, according to the production method of the present invention, the resin beads which can effectively exhibit slipperiness and soft-focus performance, which are required in resin beads to be blended in, for example, cosmetics, and which have small particle diameters can be produced.

According to the production method of the present invention, the resin beads having a solid structure in which 90% by volume or more, preferably 95% by volume or more, and still more preferably 98% by volume or more, of the inside of the solid structure is filled with the cellulose derivative can be obtained. That is, according to the production method of the present invention, the resin beads which can effectively exhibit transparency, which is required in resin beads to be blended in, for example, cosmetics, can be produced. Note that when the filling ratio (degree of solidity) of the cellulose derivatives is less than 90% by volume, light scattering occurs in empty regions, so that the transparency is likely to lower. In addition, when the degree of solidity lowers, the oil absorption changes. For this reason, when resin beads having a low degree of solidity are blended in a cosmetic, the product stability may be deteriorated.

The degree of solidity of the resin beads can be measured and calculated according to the procedure described below.

Firstly, a SEM image of sections of the resin beads, taken with a scanning electron microscope (SEM), is subjected to image analysis to calculate the volume of the part filled with the resin for each resin bead.

Subsequently, the average value of the volumes of the parts filled with the resin for 20 or more resin beads arbitrarily selected is defined as the degree of solidity (% by volume).

According to the production method of the present invention, perfectly spherical resin beads can be obtained. That is, according to production method of the present invention, the resin beads which can effectively exhibit satisfactory tactile impression and spreadability on the skin, which are required in resin beads to be blended in, for example, cosmetics, can be produced.

The degree of sphericity, which is an index of whether the resin beads have a perfectly spherical shape or not, can be measured and calculated according to the procedure described below. Firstly, a SEM image of the resin beads, taken with a scanning electron microscope (SEM), is subjected to image analysis to calculate the degree of circularity C for each resin bead from the following formula (1). Subsequently, the arithmetic average value of the degrees of circularity C for 100 or more resin beads arbitrarily selected is defined as the degree of sphericity.

$$C=(4\pi S)/(L^2) \qquad (1)$$

In the formula (1), S represents the area (projected area) of each resin bead in the image, and L represents the length of the outer peripheral part of the resin bead in the image. When the value of the degree of circularity C is closer to 1, each of the shapes of the particles is closer to a perfect sphere. In the present specification, resin beads having a degree of sphericity of 0.95 or more are defined as "perfect spheres."

According to the production method of the present invention, the resin beads having a flat surface can be obtained. According to the production method of the present invention, the resin beads which can effectively exhibit satisfactory tactile impression and spreadability on the skin, which are required in resin beads to be blended in, for example, cosmetics, can be produced.

Whether the surfaces of the resin beads are flat or not can be evaluated according to the procedure described below. That is, a SEM image (×5,000) of the resin beads, taken with a scanning electron microscope (SEM), is observed, and when the surfaces of the resin beads are flat, and unevenness and a hole are not recognized, the surfaces are evaluated as "flat," and when the surfaces are in a rough state or the like, the surfaces are evaluated as "not flat."

The resin beads which are produced by the above-mentioned production method are resin beads which have high sphericity (degree of sphericity), which are substantially solid, which have a flat surface, and which are obtained by using a natural material as a constituent material. For this reason, when the resin beads are contained, thereby various types of products, such as a cosmetic, a dermatological preparation, a paint, a shaped article, a film, a coating agent, and a resin composition, imparted with superior tactile impression, spreadability on the skin, transparency, and product stability, can be provided without using resin beads composed of a synthetic material derived from petroleum.

The resin beads of the present invention, which are produced by the above-mentioned production method, can impart properties such as superior tactile impression, spreadability on the skin, and transparency to cosmetics and the like. However, it is difficult to specify the structure, physical properties, and the like of the resin beads, corresponding to these properties, and for example, a property such as flatness needs to be assessed in a sensory manner. Further, since the resin beads are aggregates of fine particulates, an extremely large number of trials and errors are necessary to repeat over and over again various types of analysis using analysis equipment and the like and conduct statistical procedures, thereby finding out an index that specifies the characteristics of the resin beads from which desired effects are obtained, but that is far from reality.

EXAMPLES

Hereinafter, the present invention will specifically be described based on Examples, but the present invention is not limited to these Examples. Note that "part" or "parts," and "%" in Examples and Comparative Examples are each on a mass basis unless otherwise noted.
<Production of Resin Beads>

Example 1

An oil phase was prepared by dissolving 100 parts of diacetyl cellulose (trade name "CA-398-3," manufactured by Eastman Chemical Company) in 800 parts of ethyl acetate (water-solubility: 8 g/100 g). In addition, an aqueous phase was prepared by dissolving 72 parts of polyvinyl alcohol in 828 parts of ion-exchanged water. The oil phase was added to and mixed with the prepared aqueous phase, and a resultant mixture was stirred using a dissolver at 1,000 rpm for 3 minutes. The mixture was further stirred using the dissolver at 2,000 rpm for 10 minutes to obtain 1,800 parts of a suspension in which oil droplets were dispersed uniformly. The volume average particle diameter of the oil droplets, measured through observation with an optical microscope and image analysis, was 16 μm.

Ion-exchanged water in an amount of 8,200 parts was poured into 1,800 parts of the obtained suspension over 60 minutes while the suspension was being stirred using a dissolver at 500 rpm (resultant suspension: 10,000 parts, content of ethyl acetate: 8%). Subsequently, ion-exchanged water in an amount of 30,000 parts was poured into the resultant suspension over 10 minutes while the suspension was being stirred at 500 rpm, and thus a dispersion liquid of resin particles (dispersion liquid of resin beads, content of ethyl acetate: 2%) was obtained. The volume average particle diameter of the resin particles (resin beads), measured through observation with an optical microscope and image analysis, was 8 μm. The resin particles were subjected to filtration and washing, and then deflocculated in ion-exchanged water. Further, the resin particles were subjected to filtration and washing, and then dried and subjected to a cracking treatment to obtain resin beads. FIG. 1 shows an electron micrograph showing a state of surfaces of the obtained resin beads. Further, FIG. 2 shows an electron micrograph showing a state of sections of the obtained resin beads.

Example 2

An oil phase was prepared by dissolving 100 parts of diacetyl cellulose (trade name "CA-398-6," manufactured by Eastman Chemical Company) in 1,200 parts of ethylene glycol diacetate (water-solubility: 21 g/100 g). In addition, an aqueous phase was prepared by dissolving 80 parts of polyvinyl alcohol in 720 parts of ion-exchanged water, and then adding 70 parts of ethylene glycol diacetate. The oil phase was added to and mixed with the prepared aqueous phase, and a resultant mixture was stirred using a dissolver at 1,000 rpm for 3 minutes. The mixture was further stirred using the dissolver at 1,800 rpm for 10 minutes to obtain 2,170 parts of a suspension in which oil droplets were dispersed uniformly. The volume average particle diameter of the oil droplets, measured through observation with an optical microscope and image analysis, was 16 μm.

Ion-exchanged water in an amount of 3,880 parts was poured into the obtained suspension over 120 minutes while the suspension was being stirred using a dissolver at 500 rpm (resultant suspension: 6,050 parts, content of ethylene glycol diacetate: 21%). Subsequently, ion-exchanged water in an amount of 25,700 parts was poured into the resultant suspension over 30 minutes while the suspension was being stirred at 500 rpm, and thus a dispersion liquid of resin particles (dispersion liquid of resin beads, content of ethylene glycol diacetate: 4%) was obtained. The volume average particle diameter of the resin particles (resin beads), measured through observation with an optical microscope and image analysis, was 7 μm. The resin particles were subjected to filtration and washing, and then deflocculated in ion-exchanged water. Further, the resin particles were subjected to filtration and washing, and then dried and subjected to a cracking treatment to obtain resin beads.

Example 3

An oil phase was prepared by dissolving 100 parts of diacetyl cellulose (trade name "CA-398-10," manufactured by Eastman Chemical Company) in 1,000 parts of isopropyl acetate (water-solubility: 4 g/100 g). In addition, an aqueous phase was prepared by dissolving 300 parts of polyvinyl alcohol in 2,700 parts of ion-exchanged water. The oil phase was added to and mixed with the prepared aqueous phase, and a resultant mixture was stirred using a dissolver at 1,000 rpm for 3 minutes. The mixture was further stirred using the dissolver at 2,000 rpm for 10 minutes to obtain 4,100 parts of a suspension in which oil droplets were dispersed uniformly. The volume average particle diameter of the oil droplets, measured through observation with an optical microscope and image analysis, was 12 μm.

Ion-exchanged water in an amount of 22,000 parts was poured into the obtained suspension over 120 minutes while the suspension was being stirred using a dissolver at 500 rpm (resultant suspension: 26,100 parts, content of isopropyl acetate: 4%). Subsequently, ion-exchanged water in an amount of 78,300 parts was poured into the resultant suspension over 15 minutes while the suspension was being stirred at 500 rpm, and thus a dispersion liquid of resin particles (dispersion liquid of resin beads, content of isopropyl acetate: 1%) was obtained. The volume average particle diameter of the resin particles (resin beads), measured through observation with an optical microscope and image analysis, was 6 μm. The resin particles were subjected to filtration and washing, and then deflocculated in ion-exchanged water. Further, the resin particles were subjected to filtration and washing, and then dried and subjected to a cracking treatment to obtain resin beads.

Example 4

An oil phase was prepared by dissolving 100 parts of diacetyl cellulose (trade name "L-30," manufactured by Daicel Corporation) in 700 parts of ethyl acetate (water-solubility: 8 g/100 g) and 100 parts of methyl acetate (water-solubility: 23 g/100 g). In addition, an aqueous phase was prepared by dissolving 100 parts of polyvinyl alcohol in 900 parts of ion-exchanged water. The oil phase was added to and mixed with the prepared aqueous phase, and a resultant mixture was stirred using a dissolver at 1,000 rpm for 3 minutes. The mixture was further stirred using the dissolver at 2,000 rpm for 10 minutes to obtain 1,900 parts of a suspension in which oil droplets were dispersed uniformly. The volume average particle diameter of the oil droplets, measured through observation with an optical microscope and image analysis, was 24 μm.

Ion-exchanged water in an amount of 6,100 parts was poured into the obtained suspension over 60 minutes while the suspension was being stirred using a dissolver at 500 rpm (resultant suspension: 8,000 parts, total content of ethyl acetate and methyl acetate: 10%). Subsequently, ion-exchanged water in an amount of 32,000 parts was poured into the resultant suspension over 10 minutes while the suspension was being stirred at 500 rpm, and thus a dispersion liquid of resin particles (dispersion liquid of resin beads, total content of ethyl acetate and methyl acetate: 2%) was obtained. The volume average particle diameter of the resin particles (resin beads), measured through observation with an optical microscope and image analysis, was 12 μm. The resin particles were subjected to filtration and washing, and then deflocculated in ion-exchanged water. Further, the resin particles were subjected to filtration and washing, and then dried and subjected to a cracking treatment to obtain resin beads.

Example 5

An oil phase was prepared by dissolving 90 parts of diacetyl cellulose (trade name "L-50," manufactured by Daicel Corporation) and 10 parts of cellulose acetate butyrate (trade name "CAB," manufactured by Eastman Chemical Company) in 700 parts of methyl acetate (water-solubility: 23 g/100 g). In addition, an aqueous phase was prepared by dissolving 60 parts of polyvinyl alcohol in 440 parts of ion-exchanged water. The oil phase was added to and mixed with the prepared aqueous phase, and a resultant mixture was stirred using a dissolver at 1,000 rpm for 3 minutes. The mixture was further stirred using the dissolver at 2,000 rpm for 10 minutes to obtain 1,300 parts of a suspension in which oil droplets were dispersed uniformly. The volume average particle diameter of the oil droplets, measured through observation with an optical microscope and image analysis, was 19 μm.

Ion-exchanged water in an amount of 1,700 parts was poured into the obtained suspension over 60 minutes while the suspension was being stirred using a dissolver at 500 rpm (resultant suspension: 3,000 parts, content of methyl acetate: 23%). Subsequently, ion-exchanged water in an amount of 11,000 parts was poured into the resultant suspension over 12 minutes while the suspension was being stirred at 500 rpm, and thus a dispersion liquid of resin particles (dispersion liquid of resin beads, content of methyl acetate: 5%) was obtained. The volume average particle diameter of the resin particles (resin beads), measured through observation with an optical microscope and image analysis, was 10 μm. The resin particles were subjected to filtration and washing, and then deflocculated in ion-exchanged water. Further, the resin particles were subjected to filtration and washing, and then dried and subjected to a cracking treatment to obtain resin beads.

Example 6

An oil phase in which fine particle titanium oxide was dispersed was prepared by dissolving 90 parts of ethyl cellulose (trade name "ETHOCEL," manufactured by The Dow Chemical Company) in 800 parts of 1-butanol (water-solubility: 7 g/100 g), and then adding 10 parts of silicone-treated fine particle titanium oxide (trade name "MTY-110M3S," manufactured by TAYCA CORPORATION) and mixing a resultant mixture. In addition, an aqueous phase was prepared by dissolving 27 parts of hydroxypropyl methyl cellulose in 873 parts of ion-exchanged water. The oil phase was added to and mixed with the prepared aqueous phase, and a resultant mixture was stirred using a dissolver at 1,000 rpm for 3 minutes. The mixture was further stirred using the dissolver at 2,000 rpm for 10 minutes to obtain 1,800 parts of a suspension in which oil droplets were dispersed uniformly. The volume average particle diameter of the oil droplets, measured through observation with an optical microscope and image analysis, was 18 μm.

Ion-exchanged water in an amount of 10,000 parts was poured into the obtained suspension over 60 minutes while the suspension was being stirred using a dissolver at 500 rpm (resultant suspension: 11,800 parts, content of 1-butanol: 7%). Subsequently, ion-exchanged water in an amount of 41,200 parts was poured into the resultant suspension over 8 minutes while the suspension was being stirred at 500 rpm, and thus a dispersion liquid of resin particles (dispersion liquid of resin beads, content of 1-butanol: 1.5%) was obtained. The volume average particle diameter of the resin particles (resin beads), measured through observation with an optical microscope and image analysis, was 9 μm. The resin particles were subjected to filtration and washing, and then deflocculated in ion-exchanged water. Further, the resin particles were subjected to filtration and washing, and then dried and subjected to a cracking treatment to obtain resin beads.

Example 7

An oil phase in which fine particle titanium oxide was dispersed was prepared by dissolving 89 parts of cellulose acetate propionate (trade name "CAP," manufactured by Eastman Chemical Company) in 800 parts of propylene glycol monomethyl ether acetate (water-solubility: 10 g/100 g), and then adding 10 parts of fine particle titanium oxide (trade name "MT-05," manufactured by TAYCA CORPORATION) and 1 part of a dispersant (polyether-modified silicone surfactant, trade name "KF-6017," manufactured by Shin-Etsu Chemical Co., Ltd.) and mixing a resultant mixture. In addition, an aqueous phase was prepared by dissolving 50 parts of sodium polyacrylate in 850 parts of ion-exchanged water. The oil phase was added to and mixed with the prepared aqueous phase, and a resultant mixture was stirred using a dissolver at 1,000 rpm for 3 minutes. The mixture was further stirred using the dissolver at 2,500 rpm for 20 minutes to obtain 1,800 parts of a suspension in which oil droplets were dispersed uniformly. The volume average particle diameter of the oil droplets, measured through observation with an optical microscope and image analysis, was 10 μm.

Ion-exchanged water in an amount of 6,200 parts was poured into the obtained suspension over 60 minutes while the suspension was being stirred using a dissolver at 500 rpm (resultant suspension: 8,000 parts, content of propylene glycol monomethyl ether acetate: 10%).

Subsequently, ion-exchanged water in an amount of 32,000 parts was poured into the resultant suspension over 10 minutes while the suspension was being stirred at 500 rpm, and thus a dispersion liquid of resin particles (dispersion liquid of resin beads, content of propylene glycol monomethyl ether acetate: 2%) was obtained. The volume average particle diameter of the resin particles (resin beads), measured through observation with an optical microscope and image analysis, was 5 μm. The resin particles were subjected to filtration and washing, and then deflocculated in ion-exchanged water. Further, the resin particles were subjected to filtration and washing, and then dried and subjected to a cracking treatment to obtain resin beads.

Example 8

An oil phase was prepared by dissolving 71 parts of cellulose acetate propionate (trade name "CAP," manufactured by Eastman Chemical Company) in 284 parts of ethyl acetate (water-solubility: 8 g/100 g). In addition, an aqueous phase was prepared by dissolving 9 parts of polyvinyl alcohol in 236 parts of ion-exchanged water. The oil phase was added to and mixed with the prepared aqueous phase, and a resultant mixture was stirred using a large-sized dissolver at 550 rpm for 10 minutes to obtain 600 parts of a suspension in which oil droplets were dispersed uniformly. The volume average particle diameter of the oil droplets, measured through observation with an optical microscope and image analysis, was 15 μm.

Ion-exchanged water in an amount of 2,900 parts was poured into 600 parts of the obtained suspension over 100 minutes while the suspension was being stirred using a dissolver at 400 rpm (resultant suspension: 3,500 parts, content of ethyl acetate: 8%). Subsequently, ion-exchanged water in an amount of 3,500 parts was poured into the resultant suspension over 10 minutes while the suspension was being stirred at 400 rpm, and thus a dispersion liquid of resin particles (dispersion liquid of resin beads, content of ethyl acetate: 4%) was obtained. The volume average particle diameter of the resin particles (resin beads), measured through observation with an optical microscope and image analysis, was 10 μm. The resin particles were subjected to filtration and washing, and then deflocculated in ion-exchanged water. Further, the resin particles were subjected to filtration and washing, and then dried and subjected to a cracking treatment to obtain resin beads.

Example 9

An oil phase was prepared by dissolving 100 parts of diacetyl cellulose (trade name "CA-398-3," manufactured by Eastman Chemical Company) in 800 parts of ethyl acetate (water-solubility: 8 g/100 g). In addition, an aqueous phase was prepared by dissolving 72 parts of polyvinyl alcohol in 828 parts of ion-exchanged water. The oil phase was added to and mixed with the prepared aqueous phase, and a resultant mixture was stirred using a dissolver at 1,000 rpm for 3 minutes. The mixture was further stirred using the dissolver at 2,000 rpm for 10 minutes to obtain 1,800 parts of a suspension in which oil droplets were dispersed uniformly. The volume average particle diameter of the oil droplets, measured through observation with an optical microscope and image analysis, was 16 μm.

Ion-exchanged water in an amount of 8,200 parts was poured into 1,800 parts of the obtained suspension over 9 minutes while the suspension was being stirred using a dissolver at 500 rpm (resultant suspension: 10,000 parts, content of ethyl acetate: 8%). Subsequently, ion-exchanged water in an amount of 30,000 parts was poured into the resultant suspension over 10 minutes while the suspension was being stirred at 500 rpm, and thus a dispersion liquid of resin particles (dispersion liquid of resin beads, content of ethyl acetate: 2%) was obtained. The volume average particle diameter of the resin particles (resin beads), measured through observation with an optical microscope and image analysis, was 10 μm. The resin particles were subjected to filtration and washing, and then deflocculated in ion-exchanged water. Further, the resin particles were subjected to filtration and washing, and then dried and subjected to a cracking treatment to obtain resin beads.

Example 10

An oil phase was prepared by dissolving 100 parts of cellulose acetate propionate (trade name "CAP," manufactured by Eastman Chemical Company) in 500 parts of ethyl acetate (water-solubility: 8 g/100 g). In addition, an aqueous phase was prepared by dissolving 24 parts of polyvinyl alcohol in 456 parts of ion-exchanged water. The oil phase was added to and mixed with the prepared aqueous phase, and a resultant mixture was stirred using a large-sized dissolver at 500 rpm for 8 minutes to obtain 1080 parts of a suspension in which oil droplets were dispersed uniformly. The volume average particle diameter of the oil droplets, measured through observation with an optical microscope and image analysis, was 14 μm.

Ion-exchanged water in an amount of 5,170 parts was poured into 1080 parts of the obtained suspension over 6 minutes while the suspension was being stirred using a dissolver at 350 rpm (resultant suspension: 6,250 parts, content of ethyl acetate: 8%). Subsequently, ion-exchanged water in an amount of 18,750 parts was poured into the resultant suspension over 10 minutes while the suspension was being stirred at 350 rpm, and thus a dispersion liquid of resin particles (dispersion liquid of resin beads, content of ethyl acetate: 2%) was obtained. The volume average particle diameter of the resin particles (resin beads), measured through observation with an optical microscope and image analysis, was 8 μm. The resin particles were subjected to filtration and washing, and then deflocculated in ion-exchanged water. Further, the resin particles were subjected to filtration and washing, and then dried and subjected to a cracking treatment to obtain resin beads.

Comparative Example 1

Figure 3:
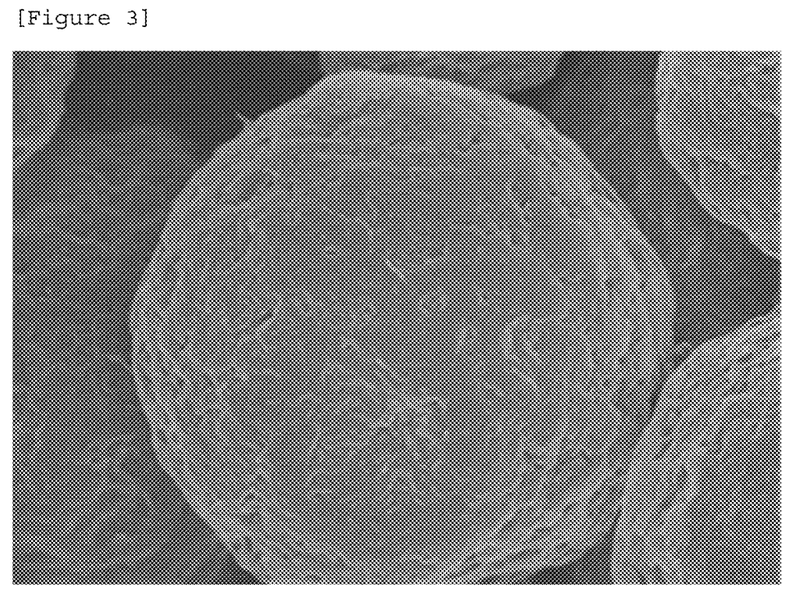
FIG. 3 is an electron micrograph showing a state of surfaces of resin beads of Comparative Example 1.

Cellulose fine particles having an average volume particle size distribution of 13 μm (trade name "CELLULOBEADS D-5," manufactured by DAITO KASEI KOGYO CO., LTD.) were used as resin beads of Comparative Example 1. FIG. 3 shows an electron micrograph showing the state of the surfaces of the resin beads of Comparative Example 1.

Comparative Example 2

An oil phase was prepared by dissolving 100 parts of diacetyl cellulose (trade name "CA-398-3," manufactured by Eastman Chemical Company) in 800 parts of ethyl acetate (water-solubility: 8 g/100 g). In addition, an aqueous phase was prepared by dissolving 72 parts of polyvinyl alcohol in 828 parts of ion-exchanged water. The oil phase was added to and mixed with the prepared aqueous phase, and a resultant mixture was stirred using a dissolver at 1,000 rpm for 3 minutes. The mixture was further stirred using the dissolver at 2,000 rpm for 10 minutes to obtain 1,800 parts of a suspension in which oil droplets were dispersed uniformly. The volume average particle diameter of the oil droplets, measured through observation with an optical microscope and image analysis, was 16 μm.

Ion-exchanged water in an amount of 8,200 parts was poured into 1,800 parts of the obtained suspension over 3 minutes while the suspension was being stirred using a dissolver at 500 rpm (resultant suspension: 10,000 parts, content of ethyl acetate: 8%). Subsequently, ion-exchanged water in an amount of 30,000 parts was poured into the resultant suspension over 10 minutes while the suspension was being stirred at 500 rpm, and thus a dispersion liquid of resin particles (dispersion liquid of resin beads, content of ethyl acetate: 2%) was obtained. The volume average particle diameter of the resin particles (resin beads), measured through observation with an optical microscope and image analysis, was 8 μm. The resin particles were subjected to filtration and washing, and then deflocculated in ion-exchanged water. Further, the resin particles were subjected to filtration and washing, and then dried and subjected to a cracking treatment to obtain resin beads.

Summary of the above-described Examples and Comparative Examples is shown in Table 1.

average value of the degrees of circularity C for 100 or more resin beads arbitrarily selected was calculated as the degree of sphericity.

$$C = (4\pi S)/(L^2) \qquad (1)$$

In the formula (1), S represents the area (projected area) of each resin bead in the image, and L represents the length of the outer peripheral part of the resin bead in the image. When the value of the degree of circularity C is closer to 1, each of the shapes of the particles is closer to a perfect sphere. The resin beads having a calculated degree of sphericity of 0.95 or more were evaluated as "perfect spheres," and the resin beads having a calculated degree of sphericity of less than 0.95 were evaluated as "non-perfect spheres." Results are shown in Table 2.

TABLE 1

Production of resin beads

| | Organic solvent | | Water (1) | | | Content of organic |
|---|---|---|---|---|---|---|
| | Suspension Weight S (parts) | Type | Water-solubility (g/100 g) | Amount W (parts) | Time required for addition (min) | (W/W)/T | solvent in suspension after addition of water (%) |
| Example 1 | 1,800 | Ethyl acetate | 8 | 8,200 | 60 | 0.076 | 8 |
| Example 2 | 2,170 | Ethylene glycol diacetate | 21 | 3,880 | 120 | 0.03 | 21 |
| Example 3 | 4,100 | Isopropyl acetate | 4 | 22,000 | 120 | 0.045 | 4 |
| Example 4 | 1,900 | Ethyl acetate Methyl acetate | 8 23 (10) | 6,100 | 60 | 0.054 | 10 |
| Example 5 | 1,300 | Methyl acetate | 23 | 1,700 | 60 | 0.022 | 23 |
| Example 6 | 1,800 | 1-Butanol | 7 | 10,000 | 60 | 0.093 | 7 |
| Example 7 | 1,800 | Propylene glycol monomethyl ether acetate | 10 | 6,200 | 60 | 0.057 | 10 |
| Example 8 | 600 | Ethyl acetate | 8 | 2,900 | 100 | 0.048 | 8 |
| Example 9 | 1,800 | Ethyl acetate | 8 | 8,200 | 9 | 0.51 | 8 |
| Example 10 | 1,080 | Ethyl acetate | 8 | 5,170 | 6 | 0.80 | 8 |
| Comparative Example 2 | 1,800 | Ethyl acetate | 8 | 8,200 | 3 | 1.52 | 8 |

<Evaluation of Resin Beads>

(Volume Average Particle Diameter)

The volume average particle diameter of the resin beads was measured using Coulter Counter (manufactured by Beckman Coulter, Inc.). Results are shown in Table 2.

(Tactile Impression)

Sensory evaluation was performed on the tactile impression of the resin beads. Specifically, the resin beads were spread on the skin and then touched. When the surface of the skin was slick, somewhat slick, not so much slick, or not slick, the tactile impression was evaluated as "good," "fair," "somewhat poor," or "poor." Results are shown in Table 2.

(Sphericity)

A SEM image of the resin beads, taken with a scanning electron microscope (SEM), was subjected to image analysis to calculate the degree of circularity C for each resin bead from the following formula (1). Subsequently, the arithmetic (Solidity)

A SEM image of sections of the resin beads, taken with a scanning electron microscope (SEM), was subjected to image analysis to calculate the volume of the part filled with the resin for each resin bead. Subsequently, the average value of the volumes of the parts filled with the resin for 20 or more resin beads arbitrarily selected was calculated as the "degree of solidity." The resin beads having a degree of solidity of 90% or more were evaluated as "solid," and the resin beads having a degree of solidity of less than 90% were evaluated as "not solid." Results are shown in Table 2.

(Flatness)

A SEM image (×5,000) of the resin beads, taken with a scanning electron microscope (SEM), was observed. When the surfaces of the resin beads were flat, the surfaces of the resin beads were evaluated as "flat," when the surfaces of the resin beads were flat, but some adsorbates were ascertained on the surfaces, the surfaces of the resin beads were evaluated as "somewhat flat," and when the surfaces of the resin beads were in a rough state, the surfaces of the resin beads were evaluated as "not flat." Note that when the surfaces of the resin beads were in the state as shown in FIG. 1, the surfaces of the resin beads were evaluated as "flat." Results are shown in Table 2.

TABLE 2

Evaluation results of resin beads

| | Volume average particle diameter (μm) | Tactile impression | Degree of sphericity | Solidity | Flatness |
|---|---|---|---|---|---|
| Example 1 | 8 | Good | Perfect spheres | Solid | Flat |
| Example 2 | 7 | Good | Perfect spheres | Solid | Flat |
| Example 3 | 6 | Good | Perfect spheres | Solid | Flat |
| Example 4 | 12 | Good | Perfect spheres | Solid | Flat |
| Example 5 | 10 | Good | Perfect spheres | Solid | Flat |
| Example 6 | 9 | Good | Perfect spheres | Solid | Flat |
| Example 7 | 5 | Good | Perfect spheres | Solid | Flat |
| Example 8 | 10 | Good | Perfect spheres | Solid | Flat |
| Example 9 | 10 | Fair | Perfect spheres | Solid | Flat |
| Example 10 | 8 | Fair | Perfect spheres | Solid | Somewhat flat |
| Comparative Example 1 | 13 | Poor | Non-perfect spheres | Not solid | Not flat |
| Comparative Example 2 | 8 | Poor | Non-perfect spheres | Not solid | Not flat |

<Production of Cosmetic>
(Cosmetic-1)

A cosmetic-1 was produced by mixing components which had conventionally been used as raw materials for cosmetics. Specifically, each of silicone-treated powders (mica, talc, fine particle titanium oxide, and barium sulfate) and the produced resin beads were blended each in the amount blended as shown in Table 3, and a resultant mixture was mixed until it became uniform to obtain a powder mixture. Subsequently, a mixture (additional components) obtained by mixing Vaseline, squalane, and glyceryl trioctanoate was added to the powder mixture, and a resultant mixture was mixed until it became uniform. Thereafter, the mixture was filled in a container, and press shaping was performed as necessary to obtain the cosmetic-1.

TABLE 3

Composition of cosmetic-1

| | Component name | Amount blended (parts) |
|---|---|---|
| Additional Components | Vaseline | 2.5 |
| | Squalane | 3.0 |
| | Glyceryl trioctanoate | 2.0 |
| Powder mixture | Silicone-treated mica | 40.0 |
| | Silicone-treated talc | 33.0 |
| | Silicone-treated fine particle titanium oxide | 5.0 |
| | Silicone-treated barium sulfate | 10.0 |
| | Resin beads of each of Examples 1 to 10 and Comparative Examples 1 and 2 | 4.5 |

(Cosmetic-2)

A cosmetic-2, which is a Sun-Cut milky lotion, was produced by mixing components which had conventionally been used as raw materials for cosmetics. Specifically, silicone oil, an ultraviolet protective agent, an emulsifier, a dispersant, isotridecyl isononanoate, and the produced resin beads were first blended and mixed each in the amount blended as shown in Table 4 to prepare oil phase components. Further, purified water, dipropylene glycol, sodium chloride, and sodium citrate were blended and mixed each in the amount blended as shown in Table 4 to prepare aqueous phase components. Subsequently, the aqueous phase components were added to the prepared oil phase components while the oil phase components were being stirred, and thus emulsification was performed to obtain the cosmetic-2.

TABLE 4

Composition of cosmetic-2

| | Component name | Amount blended (parts) |
|---|---|---|
| Aqueous phase components | Purified water | 16.8 |
| | Dipropylene glycol | 2.0 |
| | Sodium chloride | 1.0 |
| | Sodium citrate | 0.2 |
| Oil phase components | Silicone oil | 35.0 |
| | Ultraviolet protective agent | 30.0 |
| | Emulsifier | 5.0 |
| | Dispersant | 1.0 |
| | Isotridecyl isononanoate | 4.0 |
| | Resin beads of each of Examples 1 to 10 and Comparative Examples 1 and 2 | 5.0 |

<Evaluation of Cosmetics>

The tactile impression and the spreadability on the skin of the produced cosmetic-1 were evaluated according to the evaluation criteria described below. Results are shown in Table 5. In addition, the tactile impression, the spreadability on the skin, the transparency, and the product stability of the produced cosmetic-2 were evaluated according to the evaluation criteria described below. Results are shown in Table 6.

A: Excellent
B: Good
C: Fair
D: Poor

TABLE 5

Evaluation results of cosmetic-1

| Cosmetic-1 | Resin beads | Tactile impression | Spreadability on skin |
|---|---|---|---|
| Example 11 | Example 1 | A | A |
| Example 12 | Example 2 | A | A |
| Example 13 | Example 3 | A | A |
| Example 14 | Example 4 | A | A |
| Example 15 | Example 5 | A | A |
| Example 16 | Example 6 | A | A |
| Example 17 | Example 7 | A | A |
| Example 18 | Example 8 | A | A |
| Example 19 | Example 9 | B | A |
| Example 20 | Example 10 | B | B |
| Comparative Example 3 | Comparative Example 1 | C | C |
| Comparative Example 4 | Comparative Example 2 | C | C |

TABLE 6

Evaluation results of cosmetic-2

| Cosmetic-2 | Resin beads | Tactile impression | Spreadability on skin | Transparency | Product stability |
|---|---|---|---|---|---|
| Example 21 | Example 1 | A | A | A | A |
| Example 22 | Example 2 | A | A | A | A |
| Example 23 | Example 3 | A | A | A | A |

TABLE 6-continued

Evaluation results of cosmetic-2

| Cosmetic-2 | Resin beads | Tactile impression | Spreadability on skin | Transparency | Product stability |
|---|---|---|---|---|---|
| Example 24 | Example 4 | A | A | A | A |
| Example 25 | Example 5 | A | A | A | A |
| Example 26 | Example 6 | A | A | A | A |
| Example 27 | Example 7 | A | A | A | A |
| Example 28 | Example 8 | A | A | A | A |
| Example 29 | Example 9 | B | A | A | A |
| Example 30 | Example 10 | B | B | A | A |
| Comparative Example 5 | Comparative Example 1 | C | C | C | D |
| Comparative Example 6 | Comparative Example 2 | C | C | C | D |

As shown in Tables 5 and 6, it is understood that cosmetics having superior tactile impression, spreadability on the skin, transparency, and product stability were able to be produced by using the resin beads of Examples. Further, it was ascertained that properties such as superior tactile impression, transparency, spreadability, and product stability were also able to be imparted not only to a cosmetic but also to various types of products, such as a dermatological preparation, a paint, a shaped article, a film, a coating agent, and a resin composition, by using the resin beads of Examples.

INDUSTRIAL APPLICABILITY

The resin beads of the present invention have properties equal to or superior to those of the resin beads formed with a synthetic material derived from petroleum. For this reason, when the resin beads of the present invention are used, thereby products, such as cosmetics, giving satisfactory tactile impression, having good spreadability on the skin, having transparency, and having stable product quality can be provided without using resin beads formed with a synthetic material derived from petroleum. Accordingly, the resin beads of the present invention are useful as a constituent material for various types of products, such as, for example, a cosmetic, a dermatological preparation, a paint, a shaped article, a film, a coating agent, and a resin composition.

The invention claimed is:

1. A method for producing resin beads comprising a cellulose derivative as a main component, the method comprising:
preparing a suspension by mixing an oil phase comprising: the cellulose derivative, and an organic solvent that dissolves the cellulose derivative, the organic solvent having a solubility to 100 g of water (water-solubility) at 25° C. in a range from 0.1 to 50.0 g, and an aqueous phase comprising a dispersion stabilizer, thereby preparing the suspension comprising: oil droplets comprising the cellulose derivative, and the organic solvent; and
contracting the oil droplets by adding water to the suspension, thereby contracting the oil droplets,
wherein in the contracting the oil droplets, the water is added to the suspension satisfying following expression (A), until a content of the organic solvent in the suspension becomes equal to or less than the water-solubility of the organic solvent:

$(W/S)/T \leq 1.00 (A)$, wherein
W: an addition amount of water (parts by mass),
S: an amount of the suspension (parts by mass), and
T: a time (minutes) required for addition.

2. The method for producing resin beads according to claim 1,
wherein the method produces the resin beads having a degree of sphericity of 0.95 or more as measured and calculated according to a following procedure of measuring and calculating the sphericity,
wherein the procedure comprises:
subjecting a SEM image of the resin beads, taken with a scanning electron microscope, to an image analysis, and
calculating a degree of circularity C of each resin bead from following formula (1) so as to determine an arithmetic average value of the degrees of circularity C of arbitrarily selected 100 or more resin beads as the degree of sphericity of the resin beads;
$C=(4\pi S)/(L^2)(1)$, wherein S represents a projected area of each resin bead in the SEM image, and L represents a length of an outer peripheral part of the resin bead in the SEM image.

3. The method for producing resin beads according to claim 2, wherein a liquid amount of the water added to the suspension is 0.5 times or more based on a liquid amount of the suspension on a mass basis.

4. The method for producing resin beads according to claim 1, wherein the aqueous phase further comprises a second organic solvent.

5. The method for producing resin beads according to claim 1, wherein a liquid amount of the aqueous phase is in a range from 0.2 to 3.0 times or based on a liquid amount of the oil phase on a mass basis.

6. The method for producing resin beads according to claim 1, wherein the cellulose derivative is at least one material selected from the group consisting of cellulose acetate, cellulose acetate butyrate, cellulose acetate propionate, and ethyl cellulose.

7. The method for producing resin beads according to claim 1, wherein the cellulose derivative is cellulose acetate having an acetylation degree of 60% or less.

8. The method for producing resin beads according to claim 1, wherein an acetone solution comprising 6% by mass of the cellulose derivative has a viscosity of 200 mPa·s or less.

9. The method for producing resin beads according to claim 1, wherein the organic solvent is at least one solvent selected from the group consisting of a ketone-based solvent, an ester-based solvent, an alcohol, a glycol, an ether-based solvent, a halogenated alkyl, and a nitrated alkyl.

10. The method for producing resin beads according to claim 1, wherein a liquid amount of the organic solvent is 2.0 times or more based on an amount of the cellulose derivative on a mass basis.

11. The method for producing resin beads according to claim 1, wherein the dispersion stabilizer is a water-soluble polymer.

12. The method for producing resin beads according to claim 1, wherein a content of the dispersion stabilizer in the aqueous phase is 30% by mass or less.

13. The method for producing resin beads according to claim 1, wherein the resin beads having a volume average particle diameter of 50 μm or less are obtained.

14. The method for producing resin beads according to claim 1, wherein the resin beads having a solid structure in which 90% by volume or more of an inside of the solid structure is filled with the cellulose derivative are obtained.

15. The method for producing resin beads according to claim 1, wherein the oil phase further comprises at least one material selected from the group consisting of a pigment and a dye.

16. The method for producing resin beads according to claim 1, wherein the oil phase further comprises: a pigment; and at least one material selected from the group consisting of a surfactant and a polymer dispersant.

17. The method for producing resin beads according to claim 15, wherein the pigment is silicone-treated.

18. The method for producing resin beads according to claim 1, wherein the oil phase further comprises at least one material selected from the group consisting of an ultraviolet absorbing agent and an ultraviolet scattering agent.

\* \* \* \* \*